(12) United States Patent
Sakamoto et al.

(10) Patent No.: US 11,464,730 B2
(45) Date of Patent: Oct. 11, 2022

(54) COSMETIC COMPOSITION CONTAINING AQUEOUS GELLING AGENT, AND METHOD FOR PRODUCING AQUEOUS GELLING AGENT AND COSMETIC COMPOSITION

(71) Applicant: ADEKA CORPORATION, Tokyo (JP)

(72) Inventors: Takao Sakamoto, Tokyo (JP); Yasuhiro Tsushima, Tokyo (JP); Yuki Takeishi, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 301 days.

(21) Appl. No.: 16/644,031

(22) PCT Filed: Aug. 28, 2018

(86) PCT No.: PCT/JP2018/031707
§ 371 (c)(1),
(2) Date: Mar. 3, 2020

(87) PCT Pub. No.: WO2019/049725
PCT Pub. Date: Mar. 14, 2019

(65) Prior Publication Data
US 2020/0345617 A1  Nov. 5, 2020

(30) Foreign Application Priority Data
Sep. 7, 2017 (JP) .............. JP2017-172301

(51) Int. Cl.
*A61K 8/88* (2006.01)
*A61K 8/36* (2006.01)
(Continued)

(52) U.S. Cl.
CPC ............... *A61K 8/88* (2013.01); *A61K 8/361* (2013.01); *A61K 8/73* (2013.01); *A61K 8/8135* (2013.01); *A61Q 19/00* (2013.01); *A61K 2800/48* (2013.01)

(58) Field of Classification Search
CPC .......... C08L 23/02; C08L 23/12; C08L 75/08; C08L 67/02; C08L 71/02; C08L 23/10; C08L 67/00; C08L 2201/54; C08L 23/00; C08L 23/04; C08L 2666/18; C08L 67/04; C08L 101/16; C08L 2201/00; C08L 2203/16; C08L 29/04; C08L 67/025; C08K 5/3435; C08K 5/435; C08K 5/1345; C08K 5/3475; C08K 5/527; C08K 5/47; C08K 5/0083; C08K 3/34; C08K 5/134; C08K 5/523; C08K 5/529; C08K 3/11; C08K 3/18; C08K 5/0025; C08K 5/057; C08K 5/09; C08K 5/098; C08K 5/16; C08K 2201/012; C08K 3/346; C08K 5/005; C08K 5/105; C08K 5/13; C08K 5/49; C08K 5/521; C08K 9/08; C08K 2003/2244; C08K 3/011; C08K 3/013; C08K 3/16; C08K 5/092; C08K 5/315; A61K 8/042; A61K 8/87; A61K 2800/48; A61K 8/416; A61K 2800/596; A61K 8/39; A61K 8/44; A61K 8/442; A61K 8/463; A61K 8/466; A61K 8/604; A61K 8/90; A61K 2800/10; A61K 2800/5426; A61K 8/361; A61K 8/42; A61K 8/73; A61K 8/8135; A61K 8/8147; A61K 8/817; A61K 8/88; A61K 2800/87; A61K 8/046; A61K 8/345; C08G 18/283; C08G 18/4833; C08G 18/73; C08G 18/758; C08G 18/225; C08G 18/222; C08G 18/246; C08G 18/722; C08G 18/0866; C08G 18/755; C08G 2210/00; A61Q 5/00; A61Q 19/00; A61Q 19/10; A61Q 5/02; A61Q 5/06; A61Q 5/12
See application file for complete search history.

(56) References Cited

U.S. PATENT DOCUMENTS

2003/0012761 A1  1/2003  Yoshida et al.
2004/0105836 A1  6/2004  Seipel et al.
(Continued)

FOREIGN PATENT DOCUMENTS

| CN | 1383377 | 12/2002 |
|---|---|---|
| CN | 105407868 | 3/2016 |
| EP | 1 584 331 | 10/2005 |
| JP | 63-113013 | * 5/1988 ............. C08G 18/28 |
| JP | 2000-239120 | 9/2000 |
| JP | 2002-80329 | 3/2002 |

(Continued)

OTHER PUBLICATIONS

"Night Replenishing Bounceback Sleeping Mask", Database GNPD [Online] Mintel, Jul. 2017, XP055789937, Database Accession No. 4956591, 8 pages.

(Continued)

Primary Examiner — Audrea B Coniglio
(74) Attorney, Agent, or Firm — Wenderoth, Lind & Ponack, L.L.P.

(57) ABSTRACT

A cosmetic composition including component (A), which is an aqueous gelling agent represented by general formula (1) described in the specification, and a component (B), which is a polymeric thickening agent, wherein the component (A) presents a viscosity of an aqueous solution containing 1 mass % of at 25° C. of 1,000 to 5,000 mPa·s and a clouding point of the aqueous solution containing 1 mass % of component (A) of 60° C. to 80° C., and has a weight average molecular weight of 10,000 to 30,000; a method for producing the aqueous gelling agent and a method for producing the cosmetic composition are provided.

7 Claims, No Drawings

(51) Int. Cl.
*A61K 8/73* (2006.01)
*A61K 8/81* (2006.01)
*A61Q 19/00* (2006.01)

(56) References Cited

U.S. PATENT DOCUMENTS

2013/0156831 A1   6/2013   Matsuo et al.
2016/0120779 A1   5/2016   Sakamoto et al.

FOREIGN PATENT DOCUMENTS

| | | | | |
|---|---|---|---|---|
| JP | 2004-534747 | * | 11/2004 | ............... A61K 7/06 |
| JP | 2004-534747 A | * | 11/2004 | ............... A61K 8/00 |
| JP | 2010-95592 | | 4/2010 | |
| JP | 2010-95592 A | * | 4/2010 | ............... A61K 8/02 |
| JP | 2011-6371 | | 1/2011 | |
| JP | 2014-40385 | | 3/2014 | |
| JP | 2016-23180 | | 2/2016 | |

OTHER PUBLICATIONS

Extended European Search Report dated May 17, 2021 in corresponding European Patent Application No. 18853670.0.
International Search Report dated Nov. 13, 2018 in International (PCT) Application No. PCT/JP2018/031707.

* cited by examiner

COSMETIC COMPOSITION CONTAINING AQUEOUS GELLING AGENT, AND METHOD FOR PRODUCING AQUEOUS GELLING AGENT AND COSMETIC COMPOSITION

TECHNICAL FIELD

This invention relates to a cosmetic composition which has high salt resistance and temperature stability in terms of the viscosity thereof, exhibits high temporal stability upon emulsification, and imparts a favorable texture when used; a method for producing an aqueous gelling agent contained in the cosmetic composition; and a method for producing the cosmetic composition.

BACKGROUND ART

Among viscosity modifiers, natural gelling agents, such as carboxymethyl cellulose and hydroxyethyl cellulose, alkali thickening type gelling agents that are thickened by an alkali, such as poly(acrylic acid) and poly(acrylic acid)-containing copolymers, and urethane-based gelling agents, such as urethane-modified polyethers, and the like, may be listed as well-known products. Of these, urethane-based gelling agents can allow a variety of products to be gelated more freely than other gelling agents, and can impart a wide variety of viscosities to products to which such gelling agents are added, and many types of such gelling agents are produced and frequently used for reasons such as hardly being affected by ph or salts.

In particular, hydrophobically modified polyether urethanes form (soft) elastic gels having a characteristic gelatinous texture and can give gels having excellent temperature stability, and are therefore widely blended and used in a variety of cosmetics and the like (for example, see Patent Documents 1 to 4).

It is known that hydrophobically modified polyether urethanes can be used in combination with polymeric thickening agents such as carboxyvinyl polymers and xanthan gum and can give cosmetic compositions having excellent usability. For example, Patent Document 5 discloses a cosmetic composition which is characterized by containing a hydrophobically modified polyether urethane, a carboxyvinyl polymer and xanthan gum, with the hydrophobically modified polyether urethane being associated in an aqueous solvent by hydrophobic interactions.

CITATION LIST

Patent Document

[Patent Document 1] Japanese Patent Application Publication No. 2002-080329
[Patent Document 2] Japanese Patent Application Publication No. 2011-006371
[Patent Document 3] Japanese Patent Application Publication No. 2016-023180
[Patent Document 4] Japanese Patent Application Publication No. 2014-040385
[Patent Document 5] Japanese Patent Application. Publication No. 2000-239120

SUMMARY OF INVENTION

Technical Problem

However, even in cases where the cosmetic composition disclosed in Patent Document 5 exhibited satisfactory performance such as salt resistance and temperature stability in terms of the viscosity thereof, this cosmetic composition was not at a useful level in terms of all characteristics, including temporal stability upon emulsification and texture when used, and was unsatisfactory in terms of such performance.

Solution to Problem

As a result of intensive studies, the inventors of this invention discovered a cosmetic composition that exhibits improved performance compared to conventionally known cosmetic compositions, and thereby completed this invention. That is, this invention is a cosmetic composition including components (A) and (B) below, wherein the component (A) presents a viscosity of an aqueous solution containing 1 mass % of at 25° C. of 1,000 to 5,000 mPa·s and a clouding point of the aqueous solution containing 1 mass % of component (A) of 60° C. to 80° C., and has a weight average molecular weight of 10,000 to 30,000; component (A): an aqueous gelling agent represented by general formula (1) below.

$$R^2 \underset{R^1}{\overset{}{\diagdown}} \left(O - R^3\right)_a O \underset{O}{\overset{H}{\diagdown}} N - R^4 - \underset{O}{\overset{H}{\diagdown}} N \left[ \left(O - R^5\right)_d O \underset{O}{\overset{H}{\diagdown}} N - R^6 - \underset{O}{\overset{H}{\diagdown}} N \right]_g O \left(R^7 - O\right)_e \underset{R^9}{\overset{R^8}{\diagup}} \quad (1)$$

In the formula, $R^1$, $R^2$, $R^8$ and $R^9$ each independently denote a hydrocarbon group having 4 to 20 carbon atoms, $R^3$, $R^5$ and $R^7$ each independently denote a divalent hydrocarbon group having 2 to 4 carbon atoms, $R^4$ and $R^6$ each independently denote a divalent hydrocarbon group having 3 to 16 carbon atoms, a and e each independently denote a number from 10 to 100, d denotes a number from 100 to 500, and g denotes a number from 0 to 10; and
component (B): a polymeric thickening agent.

In addition, this invention provides a method for producing an aqueous gelling agent represented by general formula (1), in which compounds represented by general formulae (2) to (4) and higher fatty acid metal salts as catalysts are used, as described later.

Furthermore, this invention provides a method for producing a cosmetic composition, the method including a step of combining a polymeric thickening agent with the aqueous gelling agent obtained using the production method described above.

Advantageous Effects of Invention

This invention can provide a cosmetic composition that exhibits improved performance compared to conventionally known cosmetic compositions. Specifically, the cosmetic composition of this invention has high salt resistance and temperature stability in terms of the viscosity thereof, exhibits high temporal stability upon emulsification, and imparts a favorable texture when used.

DESCRIPTION OF EMBODIMENTS

Component (A) that constitutes the cosmetic composition of this invention is an aqueous gelling agent represented by general formula (1) below.

group, a 2-methyl-2-butenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 8-nonenyl group, a 1-decenyl group, a 9-decenyl group, a 10-undecenyl group, a 1-dodecenyl group, a 4-dodecenyl group, a 11-dodecenyl group, a 12-tridecenyl group, a 13-tetradecenyl group, a 14-pentadecenyl group, a 15-hexadecenyl group, a 16-heptadecenyl group, a 1-octadecenyl group, a 17-octadecenyl group, a 1-nonadecenyl group, and a 1-eicosenyl group;

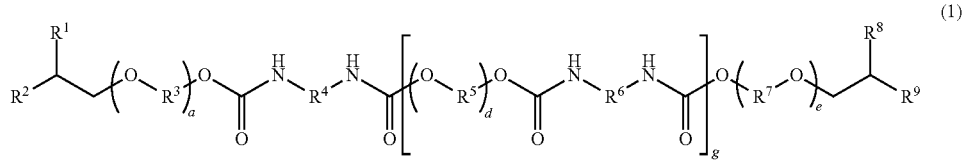

(1)

In the formula, $R^1$, $R^2$, R and $R^9$ each independently denote a hydrocarbon group having 4 to 20 carbon atoms, $R^3$, $R^5$ and $R^7$ each denote a divalent hydrocarbon group having 2 to 4 carbon atoms, $R^4$ and $R^6$ each independently denote a divalent hydrocarbon group having 3 to 16 carbon atoms, a and e each independently denote a number from 10 to 100, d denotes a number from 100 to 500, and g denotes a number from 0 to 10.

In general formula (1), $R^1$, $R^2$, $R^8$ and $R^9$ each independently denote a hydrocarbon group having 4 to 20 carbon atoms Examples of such a hydrocarbon group include saturated aliphatic hydrocarbon groups such as an n-butyl group, an isobutyl group, an s-butyl group, a t-butyl group, an n-pentyl group, a branched pentyl group, a secondary pentyl group, a tertiary pentyl group, an n-hexyl group, a branched hexyl group, an secondary hexyl group, a tertiary hexyl group, an n-heptyl group, a branched heptyl group, a secondary heptyl group, a tertiary heptyl group, an n-octyl group, a 2-ethylhexyl group, a branched octyl group, a secondary octyl group, a tertiary octyl group, an n-nonyl group, a branched nonyl group, a secondary nonyl group, a tertiary nonyl group, an n-decyl group, a branched decyl group, a secondary decyl group, a tertiary decyl group, an n-undecyl group, a branched undecyl group, a secondary undecyl group, a tertiary undecyl group, an n-dodecyl group, a branched dodecyl group, a secondary dodecyl group, a tertiary dodecyl group, an n-tridecyl group, a branched tridecyl group, a secondary tridecyl group, a tertiary tridecyl group, an n-tetradecyl group, a branched tetradecyl group, a secondary tetradecyl group, a tertiary tetradecyl group, an n-pentadecyl group, branched pentadecyl group, a secondary pentadecyl group, tertiary pentadecyl group, an n-hexadecyl group, a branched hexadecyl group, a secondary hexadecyl group, a tertiary hexadecyl group, an n-heptadecyl group, a branched heptadecyl group, a secondary heptadecyl group, a tertiary heptadecyl group, an n-octadecyl group, a branched octadecyl group, a secondary octadecyl group, a tertiary octadecyl group, an n-nonadecyl group, a branched nonadecyl group, a secondary nonadecyl group, a tertiary nonadecyl group, an n-eicosyl group, a branched eicosyl group, a secondary eicosyl group, and a tertiary eicosyl group; and unsaturated aliphatic hydrocarbon groups such as a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl aromatic hydrocarbon groups such as a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl group, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group, and a β-naphthyl group; and alicyclic hydrocarbon groups such as a cyclopropyl group, a cyclobutyl group, a cyclopentyl group, a cyclohexyl group, a cycloheptyl group, a cyclooctyl group, a methylcyclopentyl group, a methylcyclohexyl group, a methylcycloheptyl group, a methylcyclooctyl group, a 4,4,6,6-tetramethylcyclohexyl group, a 1,3-dibutylcyclohexyl group, a norbornyl group, a bicyclo[2.2.2]octyl group, an adamantyl group, a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, a 2-methyl-3-cyclohexenyl group, and a 3,4-dimethyl-3-cyclohexenyl group. In this invention, if $R^1$, $R^2$, $R^8$ and $R^9$ are not such hydrocarbon groups, it is not possible to obtain a cosmetic composition that satisfies all of the advantageous effects of this invention, and especially a cosmetic composition that exhibits high temporal stability upon emulsification cannot be obtained.

$R^1$, $R^2$, $R^8$ and $R^9$ may be the same as, or different from, each other. Of these, saturated aliphatic hydrocarbon groups and unsaturated aliphatic hydrocarbon groups are preferred, saturated aliphatic hydrocarbon groups are more preferred, saturated aliphatic hydrocarbon groups having 5 to 18 carbon atoms are further preferred, saturated aliphatic hydrocarbon groups having 8 to 14 carbon atoms are yet further preferred, and saturated aliphatic hydrocarbon groups having 10 to 12 carbon atoms are most preferred from the perspectives of readily achieving the advantageous effect of this invention, ease of procurement of raw materials and ease of production.

In general formula (1), $R^3$, $R^5$ and $R^7$ each independently denote a divalent hydrocarbon group having 2 to 4 carbon atoms. Examples of such a hydrocarbon group include an ethylene group; a propane-1,3-diyl (linear propylene) group; branched propylene groups such as a propane-1,2-diyl group and a propane-2,2-diyl group; linear butylene groups such as a butane-1,4-diyl group, a butane-1,2-diyl group, a butane-1,3-diyl group, butane-2,3-diyl group, a butane-1,1-diyl group, and a butane-2,2-diyl group; and branched butylene groups such as a 2-methylpropane-1,3-diyl group and a 2-methylpropane-1,2-diyl group. Of these, linear divalent hydrocarbon groups having 2 to 4 carbon atoms are preferred, an ethylene group and a propane-1,3-diyl (linear propylene) group are more preferred, and an ethylene group is further preferred from the perspective of readily achieving the advantageous effect of this invention. Moreover, the $R^3$ groups may all be the same as, or different from, each other, the $R^5$ groups may all be the same as, or different from, each other, and the $R^7$ groups may all be the same as, or different from, each other, In general formula (1), $R^4$ and $R^6$ each independently denote a divalent hydrocarbon group having 3 to 16 carbon atoms. Examples of such hydrocarbon groups include divalent aliphatic hydrocarbon groups having 3 to 16 carbon atoms, divalent aromatic hydrocarbon groups having 3 to 16 carbon atoms and divalent alicyclic hydrocarbon groups having 3 to 16 carbon atoms. These hydrocarbon groups may be any type as long as the number of carbon atoms falls within the range 3 to 16, but a group obtained by removing two isocyanate groups from a diisocyanate compound represented by general formula (4), which is described below, is preferred from the perspectives of ease of production and ease of procurement of raw materials. A detailed explanation of this is given later, a and e each independently denote a number from 10 to 100. Within this range, these values are preferably 12 to 50, and more preferably 15 to 30, from the perspectives of ease of production and procurement of raw materials and readily achieving the advantageous effect of this invention.

d denotes a number from 100 to 500. Within this range, the value of d is preferably 120 to 450, more preferably 150 to 400, further preferably 180 to 350, and most preferably 200 to 300, from the perspective of being able to obtain an aqueous gelling agent that can readily achieve the advantageous effect of this invention.

g denotes a number from 0 to 10. Within this range, the value of g is preferably 0 to 8, and more preferably 0 to 6, from the perspective of readily achieving the advantageous effect of this invention. Moreover, an aqueous gelling agent in which the value of g is 0 behaves like a gelling accelerator when used in combination with an aqueous gelling agent in which the value of g is 1 to 10. Therefore, from the perspective of more readily achieving the advantageous effect of this invention, a mixture of an aqueous gelling agent in which the value of g is 0 and an aqueous gelling agent in which the value of g is 1 to 10 is more preferred, a mixture of an aqueous gelling agent in which the value of g is 0 and an aqueous gelling agent in which the value of g is 1 to 8 is further preferred, and a mixture of an aqueous gelling agent in which the value of g is 0 and an aqueous gelling agent in which the value of g is 1 to 6 is most preferred.

More specifically, an aqueous gelling agent in which the mass ratio of (aqueous gelling agent in which the value of g is 1 to 10) and (aqueous gelling agent in which the value of g is 0) is 95:5 to 85:15 can exhibit the advantageous effect of this invention to the maximum extent. Moreover, an aqueous gelling agent in which the mass ratio of (aqueous gelling agent in which the value of g is 1 to 10) and (aqueous gelling agent in which the value of g is 0) is 95:5 to 85:15 can give a soft gel which has particularly good self-leveling properties and elasticity that enables use in a spray bottle, and can be advantageously used in a cosmetic requiring these effects. Moreover, "self-leveling properties" means the property of naturally returning to a level surface after a physical impact is applied to a gel (for example, after a gel is scooped out or stirred). In addition, "able to be used in a spray bottle" means a soft gel state that exhibits elasticity when housed in a spray bottle and is easily sprayed like water when sprayed from the spray bottle (when a shear stress is applied to the gel).

Component (A) contained in the cosmetic composition of this invention is an aqueous gelling agent represented by general formula (1), for which the viscosity of a 1 mass % aqueous solution at 25° C. is 1,000 to 5,000 mPa·s, the clouding point of the 1 mass % aqueous solution containing is 60° C. to 80° C., and the weight average molecular weight is 10,000 to 30,000. The method for producing component (A) must be a method by which component (A) having the properties mentioned above is obtained. This component can be synthesized in the presence of a specific catalyst using compounds represented by general formulae (2) to (4) below as raw materials.

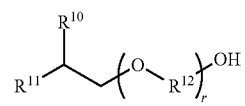

(2)

In the formula, $R^{10}$ and $R^{11}$ each independently denote a hydrocarbon group having 4 to 20 carbon atoms, $R^{12}$ denotes a divalent hydrocarbon group having 2 to 4 carbon atoms, and r denotes a number from 10 to 100.

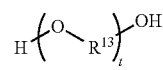

(3)

In the formula, $R^{13}$ denotes a divalent hydrocarbon group having 2 to 4 carbon atoms, and t denotes a number from 100 to 500.

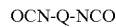

OCN-Q-NCO (4)

In the formula, Q denotes a divalent hydrocarbon group having 3 to 16 carbon atoms, In general formula (2), $R^{10}$ and $R^{11}$ each independently denote a hydrocarbon group having 4 to 20 carbon atoms. Examples of such a hydrocarbon group include saturated aliphatic hydrocarbon groups such as an n-butyl group, an isobutyl group, an s-butyl group, a t-butyl group, an n-pentyl group, a branched pentyl group, a secondary pentyl group, a tertiary pentyl group, an n-hexyl group, a branched hexyl group, a secondary hexyl group, a tertiary hexyl group, an n-heptyl group, a branched heptyl group, a secondary heptyl group, a tertiary heptyl group, an n-octyl group, a 2-ethylhexyl group, a branched octyl group, a secondary octyl group, a tertiary octyl group, an n-nonyl group, a branched nonyl group, a secondary nonyl group, a tertiary nonyl group, an n-decyl group, a branched decyl group, a secondary decyl group, a tertiary decyl group, an n-undecyl group, a branched undecyl group, a secondary undecyl group, a tertiary undecyl group, an n-dodecyl group, a branched dodecyl group, a secondary dodecyl group, a tertiary dodecyl group, an n-tridecyl group, a branched tridecyl group, a secondary tridecyl group, a tertiary tridecyl group, an n-tetradecyl group, a branched tetradecyl group, a secondary tetradecyl group, a tertiary tetradecyl group, an n-pentadecyl group, a branched pentadecyl group, a secondary pentadecyl group, a tertiary pentadecyl group, an n-hexadecyl group, a branched hexadecyl group, a secondary hexadecyl group, a tertiary hexadecyl group, an n-heptadecyl group, a branched heptadecyl group, a secondary heptadecyl group, a tertiary heptadecyl group, an n-octadecyl group, a branched octadecyl group, a secondary octadecyl group, a tertiary octadecyl group, an n-nonadecyl group, a branched nonadecyl group, a secondary nonadecyl group, a tertiary nonadecyl group, an n-icosyl group, a branched icosyl group, a secondary icosyl group, and a tertiary icosyl group; and unsaturated aliphatic hydrocarbon groups such as a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 8-nonenyl group, a 1-decenyl group, a 9-decenyl group, a 10-undecenyl group, a 1-dodecenyl group, a 4-dodecenyl group, a 11-dodecenyl group, a 12-tridecenyl group, a 13-tetradecenyl group, a 14-pentadecenyl group, a 15-hexadecenyl group, a 16-heptadecenyl group, a 1-octadecenyl group, a 17-octadecenyl group, a 1-nonadecenyl group, and a 1-icosenyl group.

aromatic hydrocarbon groups such as a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl groups, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group, and a β-naphthyl group; and alicyclic hydrocarbon groups such as a cyclopropyl group, a cyclobutyl group, a cyclopentyl group, a cyclohexyl group, a cycloheptyl group, a cyclooctyl group, a methylcyclopentyl group, a methylcyclohexyl group, a methylcycloheptyl group, a methylcyclooctyl group, a 4,4,6,6-tetramethylcyclohexyl group, a 1,3-dibutylcyclohexyl group, a norbornyl group, a bicyclo[2.2.2]octyl group, an adamantyl group, a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, a 2-methyl-3-cyclohexenyl group, and a 3,4-dimethyl-3-cyclohexenyl group.

$R^{10}$ and $R^{11}$ may be the same as, or different from, each other. Of these, saturated aliphatic hydrocarbon groups and unsaturated aliphatic hydrocarbon groups are preferred, saturated aliphatic hydrocarbon groups are more preferred, saturated aliphatic hydrocarbon groups having 5 to 18 carbon atoms are further preferred, saturated aliphatic hydrocarbon groups having 8 to 14 carbon atoms are yet further preferred, and saturated aliphatic hydrocarbon groups having 10 to 12 carbon atoms are most preferred from the perspectives of readily achieving the advantageous effect of this invention, ease of procurement of raw materials and ease of production.

In general formula (2), $R^{12}$ denotes a divalent hydrocarbon group having 2 to 4 carbon atoms. Examples of such a hydrocarbon group include an ethylene group; a propane-1,3-diyl (linear propylene) group; a branched propylene group such as a propane-1,2-diyl group and a propane-2,2-diyl group; linear butylene groups such as a butane-1,4-diyl group, a butane-1,2-diyl group, a butane-1,3-diyl group, a butane-2,3-diyl group, a butane-1,1-diyl group, and a butane-2,2-diyl group; and branched butylene groups such as a 2-methylpropane-1,3-diyl group and a 2-methylpropane-1,2-diyl group. Of these, linear divalent hydrocarbon groups having 2 to 4 carbon atoms are preferred, an ethylene group and a propane-1,3-diyl (linear propylene) group are more preferred, and an ethylene group is further preferred from the perspective of readily achieving the advantageous effect of this invention. Moreover, the $R^{12}$ groups may all be the same as, or different from, each other.

r denotes a number from 10 to 100, and within this range, the value of r is preferably a number from 12 to 50, and more preferably a number from 15 to 30, from the perspective of ease of procurement or production of a compound represented by general formula (2).

$R^{13}$ in general formula (3) denotes a divalent hydrocarbon group having 2 to 4 carbon atoms, and examples of such groups include an ethylene group; a propane-1,3-diyl (linear propylene) group; branched propylene groups such as a propane-1,2-diyl group and a propane-2,2-diyl group; linear butylene groups such as a butane-1,4-diyl group, a butane-1,2-diyl group, a butane-1,3-diyl group, a butane-2,3-diyl group, a butane-1,1-diyl group and a butane-2,2-diyl group; and branched butylene groups such as a 2-methylpropane-1,3-diyl group and a 2-methylpropane-1,2-diyl group. Of these, linear divalent hydrocarbon groups having 2 to 4 carbon atoms are preferred, an ethylene group and a propane-1,3-diyl (linear propylene) group are more preferred, and an ethylene group is further preferred from the perspective of readily achieving the advantageous effect of this invention. Moreover, the $R^{13}$ groups may all be the same as, or different from, each other.

t denotes a number from 100 to 500, and within this range, the value of t is preferably 120 to 450, more preferably 150 to 400, further preferably 180 to 350, and most preferably 200 to 300 from the perspective of readily achieving the advantageous effect of this invention.

Examples of diisocyanate compounds represented by general formula (4) include aliphatic diisocyanates such as trimethylene diisocyanate, tetramethylene diisocyanate, pentamethylene diisocyanate, hexamethylene diisocyanate (HDI), 2,2-dimethylpentane diisocyanate, octamethylene diisocyanate, 2,2,4-trimethylpentane diisocyanate, nonamethylene diisocyanate, decamethylene diisocyanate, dodecamethylene diisocyanate, isophorone diisocyanate (IPDI), dicyclohexylmethane diisocyanate (hydrogenated MDI), hydrogenated xylylene diisocyanate (hydrogenated XDI) and 2,4,4 (or 2,2,4)-trimethylhexamethylene diisocyanate (TMDI); and aromatic diisocyanates such as tolylene diisocyanate (TDI), diphenylmethane diisocyanate (MDI), toluidene diisocyanate (TODI), xylylene diisocyanate (XDI) and naphthalene diisocyanate (NDI), In general formula (4), Q may be any divalent hydrocarbon group having 3 to 16 carbon atoms, but a group obtained by removing two isocyanate groups from the diisocyanate compounds listed above is preferred. Among the diisocyanate compounds, aliphatic diisocyanates are preferred, trimethylene diisocyanate, tetramethylene diisocyanate, hexamethylene diisocyanate (HDI), octamethylene diisocyanate, isophorone diisocyanate (IPDI), dicyclohexylmethane diisocyanate (hydrogenated MDI), hydrogenated xylylene diisocyanate (hydrogenated XDI) and 2,4,4 (or 2,2,4)-trimethylhexamethylene diisocyanate (TMDI) are more preferred, tetramethylene diisocyanate, hexamethylene diisocyanate (HDI), isophorone diisocyanate (IPDI) and dicyclohexylmethane diisocyanate (hydrogenated MDI) are further preferred, and hexamethylene diisocyanate (HDI) is most preferred.

Moreover, in general formula (1) above, $R^4$ and $R^6$ each independently denote a divalent hydrocarbon group having 3 to 16 carbon atoms. More specifically, groups obtained by removing two isocyanate groups from the diisocyanate compounds listed above are preferred, groups obtained by removing two isocyanate groups from aliphatic diisocyanates are more preferred, groups obtained by removing two isocyanate groups from any of trimethylene diisocyanate, tetramethylene diisocyanate, hexamethylene diisocyanate (HDI), octamethylene diisocyanate, isophorone diisocyanate (IPDI), dicyclohexylmethane diisocyanate (hydrogenated MDI), hydrogenated xylylene diisocyanate (hydrogenated XDI) and 2,4,4 (or 2,2,4)-trimethylhexamethylene diisocyanate (TMDI) are further preferred, groups obtained by removing two isocyanate groups from any of tetramethylene diisocyanate, hexamethylene diisocyanate (HDI), isophorone diisocyanate (IPDI) and dicyclohexylmethane diisocyanate (hydrogenated MDI) are yet further preferred, and a group obtained by removing two isocyanate groups from hexamethylene diisocyanate (HDI) is most preferred.

Examples of specific catalysts used when producing component (A) include higher fatty acid metal salts selected from among lauric acid metal salts, myristic acid metal salts, palmitic acid metal salts, stearic acid metal salts and oleic acid metal salts, and it is possible to use one or more types of these. Moreover, metal salts mean any of calcium salts, potassium salts, sodium salts and magnesium salts. Of these, lauric acid metal salts are preferred, and potassium laurate and sodium laurate are more preferred, from the perspective of being able to produce an aqueous gelling agent that exhibits an advantageous effect of this invention to a remarkable extent.

In general, an aqueous gelling agent represented by general formula (1) can be produced with or without using a catalyst. In cases where a catalyst is used, it is possible to use a metal halide such as titanium tetrachloride, hafnium chloride, zirconium chloride, aluminum chloride, gallium chloride, indium chloride, iron chloride, tin chloride or boron fluoride; an alkali metal or alkaline metal hydroxide, alcoholate or carbonate, such as sodium hydroxide, potassium hydroxide, sodium methylate, or sodium carbonate; a metal oxide such as aluminum oxide, calcium oxide, barium oxide or sodium oxide; an organometallic compound such as tetraisopropyl titanate, dibutyltin dichloride, dibutyltin oxide, dibutyltin dilaurate or dibutyltin bis(2-ethylhexylthioglycolate); or a soap such as sodium octylate or potassium octylate. However, an aqueous gelling agent represented by general formula (1), for which the viscosity of an aqueous solution containing 1 mass % of component (A) at 25° C. is 1,000 to 5,000 mPa·s, the clouding point of the aqueous solution containing 1 mass % of component (A) is 60° C. to 80° C., and the weight average molecular weight of component (A) is 10,000 to 30,000, can be obtained using the higher fatty acid metal salts mentioned above. In cases where a catalyst is not used or in cases where a catalyst other than a higher fatty acid metal salt is used, the viscosity of a 1 mass % aqueous solution, the clouding point of a 1 mass % aqueous solution and the weight average molecular weight might, in some cases, deviate from the specifications of component (A) of this invention.

As to the amount of the higher fatty acid metal salt to be used as a catalyst, the higher fatty acid metal salt may be used at a quantity of 0.01 to 5 mass % relative to the overall quantity of the reaction system for the production of component (A). Within this range, the higher fatty acid metal salt is preferably used at a quantity of 0.1 to 2 mass %, and more preferably 0.5 to 1 mass %, relative to the overall reaction system from the perspective of satisfactorily achieving a significant advantageous effect. If this quantity is less than 0.01 mass %, the function of the catalyst is not sufficiently exhibited and component (A) used in this invention might not be obtained, and if this quantity exceeds 5 mass %, an advantageous effect commensurate with the added quantity might not be achieved. Moreover, a removal step is not carried out following production of component (A) in this invention, and the catalyst remains in the cosmetic containing components (A) and (B) of this invention, and the remaining quantity of catalyst depends on the usage quantity of the catalyst in the production of component (A) and the blending quantity of component (A) in the cosmetic composition described below.

A method for synthesizing component (A) in the presence of a specific catalyst using compounds represented by general formulae (2) to (4) listed above as raw materials can be given as an example of a method for producing component (A). For example, a reaction should be carried out after adding 1.5 to 2.4 moles, preferably 1.8 to 2.2 moles, and more preferably 1.9 to 2.1 moles, of an alcohol compound represented by general formula (2), 0.5 to 1.4 moles, preferably 0.8 to 1.2 moles, and more preferably 0.9 to 1.1 moles, of a polyalkylene glycol represented by general formula (3) and a catalyst to 2 moles of a diisocyanate compound represented by general formula (4). An example of a method includes one in which specific reaction conditions are such that the diisocyanate compound represented by general formula (4), the alcohol compound represented by general formula (2) and the polyalkylene glycol represented by general formula (3) are added to the system together with the catalyst and allowed to react for 1 to 10 hours at 60° C. to 100° C. An example of a method includes one in which more specific reaction conditions are such that a system containing the alcohol compound represented by general formula and the polyalkylene glycol represented by general formula (3) is homogeneously mixed, after which the diisocyanate compound represented by general formula and the catalyst are added and allowed to react for 1 to 10 hours at 60° C. to 100° C.

The viscosity of an aqueous solution containing 1 mass % of component (A), which is contained in the cosmetic composition of this invention, at 25° C. is 1,000 to 5,000 mPa·s. Within this range, the viscosity is preferably 1,500 to 4,000 mPa·s, and more preferably 2,000 to 3,500 mPa·s, from the perspective of achieving the advantageous effect of this invention to a more remarkable extent. A viscosity measurement method using a B type viscometer at 25° C., as described in JIS Z 8803: 2011, can be used as a method for measuring the viscosity of the 1 mass % aqueous solution at 25° C.

The clouding point of the aqueous solution containing 1 mass % of component (A), which constitutes the cosmetic composition of this invention, is 60° C. to 80° C. Within this range, the clouding point is preferably 60° C. to 70° C. from the perspective of achieving the advantageous effect of this invention to a more remarkable extent. A method comprising preparing a 1 mass % aqueous solution of component (A), gradually increasing the temperature of the aqueous solution, and taking the clouding point to be the temperature at which turbidity occurs can be used as a method for measuring the clouding point.

The weight average molecular weight of component (A), which constitutes the hair cosmetic composition of this invention, is 10,000 to 30,000. Within this range, the weight average molecular weight is preferably 12,000 to 25,000, and more preferably 15,000 to 20,000, from the perspective of achieving the advantageous effect of this invention to a more remarkable extent. A method comprising measuring the weight average molecular weight in terms of standard polystyrene using gel permeation chromatography (GPC) can be used as a method for measuring the weight average molecular weight. In this invention, by incorporating component (A) whose weight average molecular weight falls within this range, it is possible to obtain a hair cosmetic composition that satisfies all of the advantageous effects of this invention, and possible to obtain, in particular, a cosmetic composition that exhibits high temporal stability upon emulsification.

Component (A) contained in the cosmetic composition of this invention is a solid or viscous substance at room temperature. From the perspective of ease of handling when blended in a cosmetic, it is preferable to first dissolve component (A) in a solvent such as water so as to obtain a liquid. The amount of solvent is not particularly limited, but from the perspective of ease of handling, this quantity is preferably such that the content of component (A) is 10 to 50 mass %, and more preferably 15 to 40 mass %.

Examples of solvents able to be used include water and volatile primary alcohol compounds such as methanol, ethanol and propanol. Meanwhile, because use of volatile solvents may be restricted according to the site of use, water is most preferred among these solvents.

The blending quantity of component (A) contained in the cosmetic composition of this invention is not particularly limited, but is preferably 0.05 to 20 mass %, more preferably 0.1 to 10 mass %, further preferably 0.5 to 5 mass %, and most preferably 1 to 3 mass %, relative to the overall quantity of the cosmetic composition in order to form an aqueous gel that can readily achieve the advantageous effect of this invention, Component (B) contained in the cosmetic composition of this invention is a polymeric thickening agent. Component (B) is not particularly limited as long as this component is a polymeric thickening agent well-known in the cosmetic industry (note that the compound represented by general formula (1) above does not correspond to a polymeric thickening agent). Examples of polymeric thickening agents suitable for use in the cosmetic composition of this invention include synthetic polymeric thickening agents such as carboxyvinyl polymers, alkyl acrylate/methacrylate copolymers, poly(vinyl alcohol), polyvinylpyrrolidone, poly(methyl vinyl ether), sodium polyacrylate, polyacrylamide, polyethylene oxide) and ethylene oxide/propylene oxide block copolymers; natural polymeric thickening agents such as guar gum, locust bean gum, quince seed, carrageenan, galactan, gum Arabic, gum tragacanth, pectin, mannan, starch, xanthan gum, dextran, succinoglycan, curdlan, hyaluronic acid, gelatin, albumin, collagen, cellulose, chondroitin sulfate, dermatan sulfate, glycogen, heparan sulfate, keratan sulfate, chondroitin, mucoitin sulfate, keratosulfate and calonic acid; and semi-synthetic polymeric thickening agents such as methyl cellulose, ethyl cellulose, hydroxyethylcellulose, cationic cellulose, methylhydroxypropyl cellulose, hydroxypropyl cellulose, carboxymethyl cellulose, soluble starch, carboxymethyl starch, methylhydroxypropyl starch, methyl starch, hydroxypropyl xanthan gum, cationic guar gum, propylene glycol alginate and alginic acid salts (for example, sodium salt). Of these, synthetic polymeric thickening agents and natural polymeric thickening agents are preferred, and carboxyvinyl polymers are most preferred among synthetic polymeric thickening agents and xanthan gum is most preferred among natural polymeric thickening agents from the perspective of readily achieving the advantageous effect of this invention.

Moreover, the polymeric thickening agent used in this invention is not particularly limited, but the weight average molecular weight thereof is preferably 10,000 to 10,000,000, more preferably 40,000 to 5,000,000, and further preferably 100,000 to 2,000,000 from the perspective of readily achieving the advantageous effect of this invention.

It is possible to blend one or more types of polymeric thickening agent, which is component (B) contained in the cosmetic composition of this invention. The blending quantity thereof is not particularly limited, but is preferably 0.005 to 10 mass %, more preferably 0.01 to 5 mass %, further preferably 0.05 to 5 mass %, and most preferably 0.1 to 2 mass %, relative to the overall quantity of the cosmetic composition from the perspective of readily achieving the advantageous effect of this invention.

The blending ratio of component (A) and component (B) is not particularly limited, but the mass ratio of component (A) to component (B) is preferably 1:0.001 to 1:50, more preferably 1:0.01 to 1:30, and further preferably 1:0.05 to 1:10, from the perspective of readily achieving the advantageous effect of this invention.

The cosmetic composition of this invention may contain other additives commonly used in cosmetic compositions in order to impart a variety of characteristics as appropriate within qualitative and quantitative ranges that do not impair the advantageous effect of this invention, Examples thereof include powder components, liquid oils/fats, ester oils, silicone oils, solid oils/fats, waxes, hydrocarbon oils, higher fatty acids, higher alcohols, polyol compounds, non-ionic surfactants, cationic surfactants, anionic surfactants, amphoteric surfactants, humectants, metal ion sequestering agents, sugars (excluding polysaccharides), amino acids and derivatives thereof, organic amines, pH adjusting agents, antioxidants, preservatives, blood circulation promoters, antiphlogistic agents, activators, whitening agents, antiseborrheic agents, anti-inflammatory agents, and a variety of extracts, and one or more types of these can be blended according to need.

Examples of powder components include inorganic powders (for example, talc, kaolin, mica, sericite, muscovite, phlogopite, synthetic mica, red mica, biotite, vermiculite, magnesium carbonate, calcium carbonate, aluminum silicate, barium silicate, calcium silicate, magnesium silicate, strontium silicate, metal tungstates, magnesium, silica, zeolites, barium sulfate, calcined calcium sulfate (calcined gypsum), calcium phosphate, fluorapatite, hydroxyapatite, ceramic powders, metal soaps (for example, zinc myristate, calcium palmitate and aluminum stearate), boron nitride, and the like); organic powders (for example, polyamide resin powders (nylon powders), polyethylene powders, poly(methyl methacrylate) powders, polystyrene powders, styrene-acrylic acid copolymer resin powders, benzoguanamine resin powders, polytetrafluoroethylene powders, cellulose powders, and the like); inorganic white pigments (for example, titanium dioxide, zinc oxide, and the like); inorganic red pigments (for example, iron oxide (red iron oxide), iron titanate, and the like); inorganic brown pigments (for example, γ-iron oxide and the like); inorganic yellow pigments (for example, yellow iron oxide, loess, and the like); inorganic black pigments (for example, black iron oxide, lower-order titanium oxides, and the like); inorganic violet pigments (for example, manganese violet, cobalt violet, and the like); inorganic green pigments (for example, chromium oxide, chromium hydroxide, cobalt titanate, and the like); inorganic blue pigments (for example, ultramarine blue, Prussian blue, and the like); pearlescent pigments (for example, titanium oxide-coated mica, titanium oxide-coated bismuth oxychloride, titanium oxide-coated talc, colored titanium oxide-coated mica, bismuth oxychloride, fish scales, and the like); metal powder pigments (for example, aluminum powders, copper powders, and the like); organic pigments such as zirconium, barium and aluminum lakes (for example, organic pigments such as Red 201, Red 202, Red 204, Red 205, Red 220, Red 226, Red 228, Red 405, Orange 203, Orange 204, Yellow 205, Yellow 401 and Blue 404; Red 3, Red 104, Red 106, Red 227, Red 230, Red 401, Red 505, Orange 205, Yellow 4, Yellow 5, Yellow 202, Yellow 203, Green 3, Blue 1, and the like); and natural dyes (for example, chlorophyll, β-carotene, and the like).

Examples of liquid oils/fats include avocado oil, camellia oil, turtle oil, macadamia nut oil, corn oil, mink oil, olive oil, rape seed oil, egg yolk oil, sesame oil, persic oil, wheat germ oil, sasanqua oil, castor oil, linseed oil, safflower oil, cottonseed oil, perilla oil, soy bean oil, peanut oil, tea seed oil, kaya oil, rice bran oil, Chinese tung oil, Japanese tung oil, jojoba oil, germ oil, and triglycerides.

Examples of ester oils include isopropyl myristate, octyldodecyl myristate, isopropyl isostearate, isononyl isononanoate, isotridecyl isononanoate, butyl stearate, oleyl oleate, octyldodecyl ricinoleate, octyl hydroxystearate, ethylhexyl para-methoxycinnamate, neopentyl glycol dicaprate, propylene glycol dicaprate, diisostearyl malate, polyglyceryl diisostearate, polyglyceryl triisostearate, glyceryl diisostearate, glyceryl triisostearate, glyceryl tri(caprylate/caprate), glyceryl trihexanoate, glyceryl tri-2-ethylhexanoate, trimethylolpropane tri-2-ethylhexanoate, trimethylolpropane triisostearate, dl-α-tocopherol, dl-α-tocopherol nicotinate, pentaerythrityl tetraoctanoate, and dipentaerythrityl tripolyhydroxystearate.

Examples of silicone oils include polysiloxanes, dimethylpolysiloxanes, dimethicone, methylphenylpolysiloxanes, cyclic dimethicone, amino-modified silicones, carbinol-modified silicones, methacrylic-modified silicones, mercapto-modified silicones, phenol-modified silicones, polyether-modified silicones, methylstyryl-modified silicones, alkyl-modified silicones, and higher fatty acid ester-modified silicones.

Examples of solid oils/fats include cocoa butter, coconut oil, hydrogenated coconut oil, palm oil, palm kernel oil, Japan wax kernel oil, hydrogenated oils, Japan wax, and hydrogenated castor oil.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugar cane wax, isopropyl lanolin fatty acids, hexyl laurate, reduced lanolin, jojoba wax, hard lanolin, shellac wax, POE lanolin alcohol ethers, POE lanolin alcohol acetates, POE cholesterol ethers, polyethylene glycol lanolate, and POE hydrogenated lanolin alcohol ethers.

Examples of hydrocarbon oils include liquid paraffin, ozokerite, squalane, pristane, paraffin, ceresin, squalene, Vaseline, and microcrystalline waxes.

Examples of higher fatty acids include decanoic acid, lauric acid, myristic acid, palmitic acid, stearic acid, behenic acid, oleic acid, undecylenic acid, tall oil fatty acids, 12-hydroxystearic acid, isostearic acid, linolic acid, linolenic acid, eicosapentaenoic acid (EPA), and docosahexaenoic acid (DHA).

Examples of higher alcohols include linear alcohols such as decyl alcohol, lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyltetradecyl alcohol, lanolin alcohol, cholesterol, phytosterols, hexyldodecanol, isostearyl alcohol, and octyldodecanol.

Examples of polyol compounds include ethylene glycol, propylene glycol, butylene glycol, glycerin, diethylene glycol, dipropylene glycol, and sugar alcohols.

Examples of non-ionic surfactants include sorbitan fatty acid esters (for example, sorbitan monooleate, sorbitan monoisostearate, sorbitan monolaurate, sorbitan monopalmitate, sorbitan monostearate, sorbitan sesquiolate, sorbitan trioleate, diglycerol sorbitan penta-2-ethylhexanoate, diglycerol sorbitan tetra-2-ethylhexanoate, and the like); glycerol/polyglycerol fatty acids (for example, glycerol mono-cottonseed oil fatty acids, glycerol monoerucate, glycerol sesquioleate, glycerol monostearate, glycerol POE-monostearate, polyglycerol monoisostearate, glycerol α,α'-oleate pyroglutamate, glycerol monostearate malate, and the like); propylene glycol fatty acid esters (for example, propylene glycol monostearate and the like); hydrogenated castor oil derivatives; glycerol/polyglycerol alkyl ethers (for example, polyglyceryl/polyoxybutylene stearyl ether and the like); POE-sorbitan fatty acid esters (for example, POE-sorbitan monooleate, POE-sorbitan monostearate, POE-sorbitan tetraoleate, and the like); POE sorbitol fatty acid esters (for example, POE-sorbitol monolaurate, POE-sorbitol monooleate, POE-sorbitol pentaoleate, POE-sorbitol monostearate, and the like); POE-glycerin fatty acid esters (for example, POE-glycerin monostearate, POE-glycerin monoisostearate, POE-glycerin triisostearate); and POE-difatty acid esters (for example, POE-distearate, POE-dioleate, and the like); POE-alkyl ethers (for example, POE-lauryl ether, POE-oleyl ether, POE-stearyl ether, POE-behenyl ether, POE-2-octyldodecyl ether, POE-cholestanol ether, and the like); pluronic surfactants (for example, Pluronic and the like); POE/POP-alkyl ethers (for example, POE/POP-lauryl ether, POE/POP-cetyl ether, POE/POP-2-decyltetradecyl ether, POE/POP-monobutyl ether, POE/POP-hydrogenated lanolin, POE/POP-glycerin ether, and the like); tetra POE/tetra POP-ethylenediamine condensates (for example, Tetronic surfactants and the like); POE-castor oil/hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, POE-hydrogenated castor oil maleate, and the like); POE beeswax/lanolin derivatives (for example, POE sorbitol beeswax and the like); alkanolamides (for example, coconut oil fatty acid diethanolamide, coconut oil fatty acid monoethanolamide, lauric acid monoethanolamide, fatty acid isopropanolamides, and the like); POE-propylene glycol fatty acid esters; POE alkylamines; N-methylalkylglucamides (for example, N-methyllaurylglucamide and the like); N-polyhydroxyalkyl fatty acid amides; POE-fatty acid amides; sucrose fatty acid esters (for example, sucrose monostearate, sucrose monolaurate, POE-sucrose monolaurate, and the like); alkylethoxydimethylamine oxides; and trioleylphosphonic acid. Moreover, POE is an abbreviation of polyoxyethylene, and POP is an abbreviation of polyoxypropylene, Examples of cationic surfactants include alkyltrimethyl ammonium salts such as cetyltrimethyl ammonium chloride, stearyltrimethyl ammonium chloride, lauryltrimethyl ammonium chloride, behenyltrimethyl ammonium chloride and behenyltrimethyl ammonium methosulfate; alkyltriethyl ammonium salts such as cetyltriethyl ammonium chloride, stearyltriethyl ammonium chloride, lauryltriethyl ammonium chloride, behenyltriethyl ammonium chloride, cetyltriethyl ammonium methosulfate, and behenyltriethyl ammonium methosulfate; dialkyldimethyl ammonium salts such as distearyldimethyl ammonium chloride, dicetyldimethyl ammonium chloride, dilauryldimethyl ammonium chloride and stearyldimethylbenzyl ammonium chloride; alkoxyalkyltrimethyl ammonium salts such as stearoxypropyltrimethyl ammonium chloride, stearoxyethyltrimethyl ammonium chloride and stearoxyhydroxypropyltrimethyl ammonium chloride; salts produced by reacting an alkyldimethylamine, such as N,N-dimethylbehenylamine or N,N-dimethylstearylamine, with an organic acid or inorganic acid; salts produced by reacting an alkoxydimethylamine, such as N,N-dimethyl-3-hexadecyloxypropylamine or N,N-dimethyl-3-octadecyloxypropylamine, with an organic acid or inorganic acid; and amide compounds such as diethylaminoethyl stearic acid amide, dimethylaminoethyl stearic acid amide, diethylaminoethyl palmitic acid amide, dimethylaminoethyl palmitic acid amide, diethylaminoethyl myristic acid amide, dimethylaminoethyl myristic acid amide, diethylaminoethyl behenic acid amide, dimethylaminoethyl behenic acid amide, diethylaminopropyl stearic acid amide, dimethylaminopropyl stearic acid amide, diethylaminopropyl palmitic acid amide, dimethylaminopropyl palmitic acid amide, diethylaminopropyl myristic acid amide, dimethylaminopropyl myristic acid amide, diethylaminopropyl behenic acid amide and dimethylaminopropyl behenic acid amide.

Examples of anionic surfactants include higher fatty acid salt-based surfactants, sulfonic acid salt-based surfactants, sulfate ester salt-based surfactants, phosphate ester salt-based surfactants and sulfosuccinic acid salt-based surfactants. Examples of higher fatty acid salt-based surfactants include salts (potassium salts, sodium salts, triethanolamine salts, ammonium salts, and the like) of saturated or unsaturated fatty acids having 12 to 18 carbon atoms, coconut oil fatty acid, hydrogenated coconut oil fatty acid, palm oil fatty acid, hydrogenated palm oil fatty acid, beef tallow fatty acid, hydrogenated beef tallow fatty acid, and the like; alkyl ether carboxylic acid salts, alkyl allyl ether carboxylic acid salts, N-acylsarcosine salts, and N-acylglutamic acid salts. Specific examples thereof include potassium laurate, sodium laurate, sodium palmitate, potassium myristate, sodium lauryl ether carboxylate, sodium N-lauroylsarcosinate, sodium N-lauroylglutamate, sodium coconut oil fatty acid glutamate, disodium N-stearoylglutamate, monosodium N-myristoyl-L-glutamate, sodium coconut oil fatty acid isethionate, and triethanolamine coconut oil fatty acid.

Examples of sulfonic acid salt-based surfactants include higher fatty acid amide sulfonic acid salts, alkylbenzene sulfonic acid salts, N-acylamino sulfonic acid salts, α-olefin sulfonic acid salts, and higher fatty acid ester sulfonic acid salts. Specific examples thereof include sodium N-myristoyl-N-methyltaurine, sodium N-stearoyl-N-methyltaurine, sodium coconut oil fatty acid methyltaurine, sodium coconut oil fatty acid acylmethyltaurine, sodium laurylmethyltaurine, sodium dodecylbenzene sulfonate, triethanolamine dodecylbenzene sulfonate, and sodium N-cocoyl-N-methyltaurine.

Examples of sulfate ester-based surfactants include higher alkyl sulfates, polyoxyethylene alkyl ether sulfates, higher fatty acid ester sulfates, secondary alcohol sulfates, and higher fatty acid alkylolamide sulfates. Specific examples thereof include sodium lauryl sulfate, potassium lauryl sulfate, triethanolamine polyoxyethylene lauryl sulfate, sodium polyoxyethylene lauryl sulfate, and sodium hydrogenated coconut oil fatty acid glycerin sulfate.

Examples of phosphate ester-based surfactants include triethanolamine monolauryl phosphate, dipotassium monolauryl phosphate, sodium polyoxyethylene oleyl ether phosphate, and sodium polyoxyethylene stearyl ether phosphate. Examples of sulfosuccinic acid salt-based surfactants include sodium polyoxyethylene alkyl sulfosuccinates, sodium di-2-ethylhexyl sulfosuccinate, sodium monolauroyl monoethanolamide polyoxyethylene sulfosuccinate, and sodium lauryl polypropylene glycol sulfosuccinate.

Examples of amphoteric surfactants include imidazoline-based amphoteric surfactants, betaine-based amphoteric surfactants, acyl tertiary amine oxides, and acyl tertiary phosphine oxides.

Examples of imidazoline-based amphoteric surfactants include sodium 2-undecyl-N,N,N-(hydroxyethylcarboxymethyl)-2-imidazoline, and 2-cocoyl-2-imidazolinium hydroxide-1-carboxyethyloxy disodium salt.

Examples of betaine-based amphoteric surfactants include alkylbetaines, alkylamidobetaines, alkylsulfobetaines, alkylhydroxysulfobetaines, and phosphobetaines. Specific examples thereof include lauryl dimethylamino acetic acid betaine, myristyl dimethylamino acetic acid betaine, coconut oil fatty acid amidopropyl betaine, coconut oil fatty acid dimethylsulfopropyl betaine, lauryldimethylaminohydroxysulfo betaine, laurylhydroxyphosphobetaine, 2-heptadecyl-N-carboxymethyl-N-hydroxyethyl imidazolinium betaine, and coconut oil alkyl-N-hydroxyethyl imidazolinium betaine.

Examples of acyl tertiary amine oxides include lauryldimethylamine oxide. Examples of acyl tertiary phosphine oxides include lauryldimethylphosphine oxide.

Examples of humectants include polyethylene glycol, xylitol, sorbitol, maltitol, chondroitin sulfate, hyaluronic acid, mucoitin sulfate, calonic acid, atelocollagen, cholesteryl-12-hydroxystearate, sodium lactate, bile salts, dl-pyrrolidone carboxylic acid salts, short chain soluble collagen, diglycerol (EO)PO adducts, Rosa roxburghii extract, Achillea millefolium extract, and melilot extract.

Examples of metal ion-sequestering agents include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid and trisodium ethylenediamine hydroxyethyl triacetate.

Examples of monosaccharides include trioses (for example, D-glyceryl aldehyde, dihydroxyacetone, and the like); tetroses (for example, D-erythrose, D-erythrulose, D-threose, erythritol, and the like); pentoses (for example, L-arabinose, D-xylose, L-lyxose, D-arabinose, D-ribose, D-ribulose, D-xylulose, L-xylulose, and the like); hexoses (for example, D-glucose, D-talose, D-psicose, D-galactose, D-fructose, L-galactose, L-mannose, D-tagatose, and the like); heptoses (for example, aldoheptose, hepulose, and the like); octoses (for example, octulose and the like); deoxy sugars (for example, 2-deoxy-D-ribose, 6-deoxy-L-galactose, 6-deoxy-L-mannose, and the like); amino sugars (for example, D-glucosamine, D-galactosamine, sialic acid, aminouronic acid, muramic acid, and the like); uronic acids (for example, D-glucuronic acid, D-mannuronic acid, L-guluronic acid, D-galacturonic acid, L-iduronic acid, and the like).

Examples of oligosaccharides include sucrose, umbelliferose, lactose, planteose, isolychnose, α,α-trehalose, raffinose, lychnose, umbilicin, stachyose and verbascose.

Examples of amino acids include neutral amino acids (for example, threonine, cysteine, and the like) and basic amino acids (for example, hydroxylysine). In addition, examples of amino acid derivatives include sodium acyl sarcosinate (sodium lauroyl sarcosinate), acyl glutamates, sodium acyl β-alanine, glutathione and pyrrolidone carboxylic acid.

Examples of organic amines include monoethanolamine, diethanolamine, triethanolamine, morpholine, triisopropanolamine, 2-amino-2-methyl-1,3-propane diol and 2-amino-2-methyl-1-propanol.

Examples of pH-adjusting agents include buffering agents such as lactic acid-sodium lactate, citric acid-sodium citrate and succinic acid-sodium succinate.

Examples of vitamins include vitamins A, B1, B2, B6, C and E and derivatives thereof, pantothenic acid and derivatives thereof, and biotin.

Examples of antioxidants include tocopherols, dibutylhydroxytoluene, butylhydroxyanisole, and gallic acid esters.

Examples of other components able to be blended include preservatives (methylparaben, ethylparaben, butylparaben, phenoxyethanol, and the like); antiphlogistic agents (for example, glycyrrhizinic acid derivatives, glycyrrhetinic acid derivatives, salicylic acid derivatives, hinokitiol, zinc oxide, allantoin, and the like); whitening agents (for example, meadow saxifrage extracts, arbutin, and the like); a variety of extracts (for example, Phellodendron amurense, Coptis japonica, Lithospermum erythrorhizon, Chinese peony, Japanese green gentian, birch, sage, Eriobotrya japonica, carrot, aloe, common mallow, iris, grape, coix seed, sponge cucumber, lily, saffron, Cnidium officinale, ginger, Hypericum erectum, Restharrows, garlic, red pepper, Citrus reticulata peel, Angelica acutiloba, seaweed, and the like); activators (for example, royal jelly, photosensitizers, cholesterol derivatives, and the like); blood circulation promoters (for example, benzyl nicotinate, β-butoxyethyl nicotinate, capsaicin, zingerone, cantharidis tincture, ichthammol, tannic acid, α-borneol, tocopherol nicotinate, inositol hexanicotinate, cyclandelate, cinnarizine, tolazoline, acetylcholine, verapamil, cepharanthine, γ-oryzanol, and the like); antiseborrheic agents (for example, sulfur, thianthol, and the like); and anti-inflammatory agents (for example, tranexamic acid, thiotaurine, hypotaurine, and the like).

The cosmetic composition of this invention can be used without particular limitation in cosmetics that require the advantageous effect of this invention, and can be used in, for example, skin cosmetic compositions.

In addition, the aqueous gelling agent represented by general formula (1) of component (A) of this invention, for which the viscosity of a 1 mass % aqueous solution at 25° C. is 1,000 to 5,000 mPa·s, the clouding point of the 1 mass % aqueous solution is 60 to 80° C., and the weight average molecular weight is 10,000 to 30,000, can be used in order to improve at least one, and preferably all, of the advantageous effects selected from among salt resistance and temperature stability in terms of viscosity, and texture when used of a cosmetic composition containing a polymeric thickening agent.

EXAMPLES

This invention will now be explained in detail by means of examples, but this invention is in no way limited to these examples, and may be altered as long as such alterations do not deviate from the scope of this invention. Moreover, in the examples etc. given below, % means mass percentage unless explicitly indicated otherwise, First, component (A) used in the examples and comparative examples was produced.

<Raw Materials Used to Produce Component (A)>

The raw materials used when producing component (A) are as follows,

Compound (2)-1: A compound in which $R^{10}$ is a decyl group, $R^{11}$ is a dodecyl group, $R^{12}$ is an ethylene group and r=20 in general formula (2)

Compound (2)-2: A compound in which $R^{10}$ is an octyl group, $R^{11}$ is a decyl group, $R^{12}$ is an ethylene group and r=20 in general formula (2)

Compound (2)-3: A compound in which $R^{10}$ is a dodecyl group, $R^{11}$ is a tetradecyl group, $R^{12}$ is an ethylene group and r=20 in general formula (2)

Compound (2)-4: A compound in which $R^{10}$ is a decyl group, $R^{11}$ is a dodecyl group, $R^{12}$ is an ethylene group and r=100 in general formula (2)

Compound (3)-1: A compound in which $R^{13}$ is an ethylene group and t=250 in general formula (3)

Compound (3)-2: A compound in which $R^{13}$ is an ethylene group and t=450 in general formula (3)

Compound (3)-3: A compound in which $R^{13}$ is an ethylene group and t=135 in general formula (3)

Compound (4)-1: Hexamethylene diisocyanate

Compound (4)-2: Dicyclohexylmethane diisocyanate (hydrogenated MDI)

Catalyst 1: Potassium laurate

Catalyst 2: Sodium laurate

Catalyst 3: Tetraisopropyl titanate

Catalyst 4: Dibutyltin dilaurate

<Method for Producing Component (A)>

620 g (0.06 moles) of compound (3)-1 and 139 g (0.11 moles) of compound (2)-1 were placed in a four neck flask equipped with a temperature gauge, a nitrogen inlet tube and a stirrer, the temperature was increased to 40 to 50° C., stirring was carried out until the components were homogeneously mixed, and once it had been confirmed that components were homogeneously mixed, 18.9 g (0.11 moles) of compound (4)-1 and 5.8 g (0.02 moles) of catalyst 1 were placed in the flask, and the system was purged with nitrogen. Component (A)-1 was then obtained by increasing the temperature to 80° C. to 90° C. and allowing a reaction to take place for 6 hours at this temperature.

Components (A)-2 to (A)-12 were produced by means of a similar method using the raw materials shown in Table 1. Moreover, components (A)-9 and (A)-10 were produced without using a catalyst, and components (A)-1 to (A)-12 were all produced using the same total mass of compound (2), compound (3) and compound (4), which are raw materials (that is, the mass of the overall reaction system),

TABLE 1

| | Raw materials | | | | Usage quantities (moles) of raw materials | | | |
|---|---|---|---|---|---|---|---|---|
| | Compound (2) | Compound (3) | Compound (4) | Catalyst | Compound (2) | Compound (3) | Compound (4) | Catalyst |
| Component (A)-1 | Compound (2)-1 | Compound (3)-1 | Compound (4)-1 | Catalyst 1 | 0.11 | 0.06 | 0.11 | 0.02 |
| Component (A)-2 | Compound (2)-2 | Compound (3)-1 | Compound (4)-1 | Catalyst 1 | 0.11 | 0.06 | 0.11 | 0.02 |
| Component (A)-3 | Compound (2)-2 | Compound (3)-3 | Compound (4)-1 | Catalyst 1 | 0.18 | 0.09 | 0.19 | 0.02 |
| Component (A)-4 | Compound (2)-3 | Compound (3)-1 | Compound (4)-1 | Catalyst 1 | 0.11 | 0.06 | 0.11 | 0.02 |
| Component (A)-5 | Compound (2)-4 | Compound (3)-1 | Compound (4)-1 | Catalyst 1 | 0.07 | 0.04 | 0.07 | 0.02 |
| Component (A)-6 | Compound (2)-1 | Compound (3)-2 | Compound (4)-1 | Catalyst 1 | 0.07 | 0.03 | 0.07 | 0.02 |
| Component (A)-7 | Compound (2)-1 | Compound (3)-1 | Compound (4)-2 | Catalyst 1 | 0.11 | 0.06 | 0.11 | 0.02 |
| Component (A)-8 | Compound (2)-1 | Compound (3)-1 | Compound (4)-1 | Catalyst 2 | 0.11 | 0.06 | 0.11 | 0.02 |
| Component (A)-9 | Compound (2)-1 | Compound (3)-1 | Compound (4)-1 | None | 0.11 | 0.06 | 0.11 | — |
| Component (A)-10 | Compound (2)-2 | Compound (3)-3 | Compound (4)-1 | None | 0.18 | 0.09 | 0.19 | — |
| Component (A)-11 | Compound (2)-1 | Compound (3)-1 | Compound (4)-1 | Catalyst 3 | 0.11 | 0.06 | 0.11 | 0.02 |
| Component (A)-12 | Compound (2)-1 | Compound (3)-1 | Compound (4)-1 | Catalyst 4 | 0.11 | 0.06 | 0.11 | 0.02 |

The constitutions and physical properties of obtained components (A)-1 to (A)-12 are shown in Table 2. Moreover, the obtained components (A) were mixtures of an aqueous gelling agent in which the value of g in general formula (1) is 1 to 10 and an aqueous gelling agent in which the value of g is 0, and the mass ratios of the aqueous gelling agents are also shown in Table 2.

Method for measuring viscosity of 1 mass % aqueous solution

Measurement samples were prepared by adding water to the obtained components (A) so as to obtain a 1 mass % aqueous solution, and the viscosity of each aqueous solution was measured at 25° C. using a B type viscometer (a TVB-10 available from Toki Sangyo Co., Ltd.).

Method for measuring clouding point of 1 mass % aqueous solution

The thus prepared 1 mass % aqueous solution of component (A) was placed in a constant temperature bath, the temperature was gradually increased (at a rate of approximately 1° C./min), and the clouding point (° C.) was taken to be the temperature at which turbidity occurred.

Method for measuring weight average molecular weight

Weight average molecular weight was measured by means of gel permeation chromatography (GPC). Detailed measurement conditions are as follows.
GPC apparatus: HLC-8220GPC (Tosoh Corporation)
Column: Five columns connected in series, namely one TSKgel guard column SuperMP (HZ)-N column and four TSKgel SuperMultipore HZ-N columns.
Detector: RI
Sample concentration: 5 mg/ml (in THF solution)
Column temperature: 40° C.
Standard sample: Polystyrene In component (A), the mass ratio of a compound in which the value of g in general formula (1) is 0 and a compound in which the value of g is 1 to 10 is calculated from the area ratio of charts obtained from the GPC mentioned above.

TABLE 2

| | Constitution of component (A) | | Physical properties of 1% aqueous solution of component (A) | |
|---|---|---|---|---|
| | Weight average molecular weight | Mass ratio* | Viscosity (mPa · s, 25° C.) | Clouding point (° C.) |
| Component (A)-1 | 20,000 | 90:10 | 3500 | 65 |
| Component (A)-2 | 18,000 | 90:10 | 1500 | 70 |
| Component (A)-3 | 11,000 | 85:15 | 1200 | 60 |
| Component (A)-4 | 22,000 | 90:10 | 3500 | 65 |
| Component (A)-5 | 25,000 | 90:10 | 3000 | 70 |
| Component (A)-6 | 29,000 | 85:15 | 3000 | 60 |
| Component (A)-7 | 20,000 | 90:10 | 3500 | 65 |
| Component (A)-8 | 20,000 | 90:10 | 3500 | 65 |
| Component (A)-9 | 15,000 | 98:2 | 800 | 85 |
| Component (A)-10 | 10,000 | 75:25 | 6100 | 50 |
| Component (A)-11 | 13,000 | 85:15 | 5500 | 55 |
| Component (A)-12 | 12,000 | 85:15 | 6000 | 53 |

*Mass ratio of (aqueous gelling agent in which value of g is 1 to 10) and (aqueous gelling agent in which value of g is 0) in general formula (1)

<Component B>

Component (B) used in the examples and comparative examples are shown below.

Component (B)-1: Carboxyvinyl polymer

Component (B)-2: Xanthan gum

<Preparation of Gel>

Next, gels were prepared by blending components (A) and (B) above at the quantities shown in Table 3 (see Table 3).

TABLE 3

|  | Example 1 Gel 1 | Example 2 Gel 2 | Example 3 Gel 3 | Example 4 Gel 4 | Example 5 Gel 5 | Example 6 Gel 6 | Example 7 Gel 7 | Example 8 Gel 8 | Example 9 Gel 9 |
|---|---|---|---|---|---|---|---|---|---|
| Component (A)-1 | 5 |  |  |  |  |  |  |  | 15 |
| Component (A)-2 |  | 5 |  |  |  |  |  |  |  |
| Component (A)-3 |  |  | 5 |  |  |  |  |  |  |
| Component (A)-4 |  |  |  | 5 |  |  |  |  |  |
| Component (A)-5 |  |  |  |  | 5 |  |  |  |  |
| Component (A)-6 |  |  |  |  |  | 5 |  |  |  |
| Component (A)-7 |  |  |  |  |  |  | 5 |  |  |
| Component (A)-8 |  |  |  |  |  |  |  | 5 |  |
| Component (A)-9 |  |  |  |  |  |  |  |  |  |
| Component (A)-10 |  |  |  |  |  |  |  |  |  |
| Component (A)-11 |  |  |  |  |  |  |  |  |  |
| Component (A)-12 |  |  |  |  |  |  |  |  |  |
| Component (B)-1 | 0.5 | 0.5 | 0.5 | 0.5 | 0.5 | 0.5 | 0.5 | 0.5 | 0.5 |
| Component (B)-2 |  |  |  |  |  |  |  |  |  |
| Purified water | Balance | Balance | Balance | Balance | Balance | Balance | Balance | Balance | Balance |
| Total | 500 | 500 | 500 | 500 | 500 | 500 | 500 | 500 | 500 |

|  | Example 10 Gel 10 | Example 11 Gel 11 | Comp. Example 1 Gel 12 | Comp. Example 2 Gel 13 | Comp. Example 3 Gel 14 | Comp. Example 4 Gel 15 | Comp. Example 5 Gel 16 | Comp. Example 6 Gel 17 | Comp. Example 7 Gel 18 |
|---|---|---|---|---|---|---|---|---|---|
| Component (A)-1 | 5 |  |  |  |  |  |  |  |  |
| Component (A)-2 |  |  |  |  |  |  |  |  |  |
| Component (A)-3 |  | 5 |  |  |  |  |  |  |  |
| Component (A)-4 |  |  |  |  |  |  |  |  |  |
| Component (A)-5 |  |  |  |  |  |  |  |  |  |
| Component (A)-6 |  |  |  |  |  |  |  |  |  |
| Component (A)-7 |  |  |  |  |  |  |  |  |  |
| Component (A)-8 |  |  |  |  |  |  |  |  |  |
| Component (A)-9 |  |  | 5 |  |  |  |  |  |  |
| Component (A)-10 |  |  |  | 5 | 5 |  |  |  |  |
| Component (A)-11 |  |  |  |  |  | 5 |  |  |  |
| Component (A)-12 |  |  |  |  |  |  | 5 |  |  |
| Component (B)-1 |  |  | 0.5 | 0.5 |  | 0.5 | 0.5 |  | 0.5 |
| Component (B)-2 | 0.5 | 0.5 |  |  | 0.5 |  |  | 0.5 |  |
| Purified water | Balance | Balance | Balance | Balance | Balance | Balance | Balance | Balance | Balance |
| Total | 500 | 500 | 500 | 500 | 500 | 500 | 500 | 500 | 500 |

Unit: g

<Gel Performance Evaluations>

Performance evaluations were carried out for the gels shown in Table 3. Evaluation criteria were (1) salt resistance in terms of viscosity, (2) temperature stability in terms of viscosity, and (3) texture when used (gelatinous texture or the like), Evaluation criteria are as described below. Viscosity measurements were carried out using a B type viscometer (a TVB-10 available from Toki Sangyo Co., Ltd.).

(1) Salt Resistance in Terms of Viscosity 0.5 g of NaCl was added to 100 g of a gel shown in Table 3, and then stirred and mixed. The viscosity at 25° C. before and after the salt was added were measured and the salt resistance in terms of viscosity was evaluated. The evaluation was carried out on the basis of the criteria below. In these evaluations, B or higher was taken to be a pass.

A: Degree of change in viscosity of less than 5%
B: Degree of change in viscosity of not less than 5% but less than 10%
C: Degree of change in viscosity of not less than 10% but less than 30%
D: Degree of change in viscosity of not less than 30% but less than 50%
E: Degree of change in viscosity of not less than 50%

(2) Temperature Stability in Terms of Viscosity 100 g of each gel shown in Table 3 was placed in transparent glass containers and stored for 2 months in constant temperature baths at temperatures of 25° C. or 50° C., The state (viscosity) of each sample was then measured at 25° C., and the difference between the viscosity of a sample stored at 25° C. (standard value) and the viscosity of a sample stored at 50° C. was calculated as the degree of change in viscosity from these results, and evaluated as A to D, as shown below. In these evaluations, B or higher was taken to be a pass, A: The degree of change in the viscosity of a sample stored at 50° C. compared to that of a sample stored at 25° C. was not more than 10%,
B: The degree of change in the viscosity of a sample stored at 50° C. compared to that of a sample stored at 25° C. was more than 10% but not more than 20%.
C: The degree of change in the viscosity of a sample stored at 50° C. compared to that of a sample stored at 25° C. was more than 20% but not more than 30%
D: The degree of change in the viscosity of a sample stored at 50° C. compared to that of a sample stored at 25° C. was more than 30%, (3) Texture When Used (Gelatinous Texture or the like)

Specifically, a good texture (a gelatinous texture or the like) when used means (I) a soft gelatinous texture when approximately 5 g of an obtained gel is placed in the palm of the hand and shaken back and forth and also (II) a soft gel that can be easily spread when this gel is spread across the skin. The gels shown in Table 3 were comprehensively evaluated in terms of items (I) and (II) above by 10 people, with the highest score being 5 points (and the lowest score being 1 point), and the total scores were evaluated as A to E using the criteria below. In these evaluations, B or higher was taken to be a pass.

A: Total score of 45 to 50 points
B: Total score of 40 to 44 points
C: Total score of 35 to 39 points
D: Total score of 30 to 34 points
E: Total score of 29 points or less

TABLE 4

|  | Salt resistance in terms of viscosity | Temperature stability in terms of viscosity | Texture when used |
| --- | --- | --- | --- |
| Example 1 | A | A | A |
| Example 2 | A | A | A |
| Example 3 | A | A | A |
| Example 4 | A | A | B |
| Example 5 | A | A | A |
| Example 6 | A | A | B |
| Example 7 | A | A | B |
| Example 8 | A | A | A |
| Example 9 | B | A | A |
| Example 10 | A | A | A |
| Example 11 | A | A | A |
| Comp. Example 1 | C | A | D |
| Comp. Example 2 | C | A | D |
| Comp. Example 3 | C | A | D |
| Comp. Example 4 | D | C | C |
| Comp. Example 5 | D | C | C |
| Comp. Example 6 | E | B | E |
| Comp. Example 7 | E | B | D |

<Preparation of Cosmetic Compositions>

Cosmetic compositions containing component (A) and component (B) (oil-in-water type emulsion compositions) were then prepared (see Tables 5 and 6). In terms of preparation method, cosmetic compositions 1 to 20 were obtained by initially blending components other than components (A) and (B) so as to prepare a base oil-in-water type emulsion composition, and then adding component (A) and component (B).

TABLE 5

|  | Example 12 Cosmetic composition 1 | Example 13 Cosmetic composition 2 | Example 14 Cosmetic composition 3 | Example 15 Cosmetic composition 4 | Example 16 Cosmetic composition 5 | Example 17 Cosmetic composition 6 | Example 18 Cosmetic composition 7 |
| --- | --- | --- | --- | --- | --- | --- | --- |
| Component (A)-1 | 5 | 15 | 5 | 5 | 5 |  |  |
| Component (A)-2 |  |  |  |  |  | 5 |  |
| Component (A)-3 |  |  |  |  |  |  | 5 |
| Component (A)-4 |  |  |  |  |  |  |  |
| Component (A)-5 |  |  |  |  |  |  |  |
| Component (A)-6 |  |  |  |  |  |  |  |
| Component (A)-7 |  |  |  |  |  |  |  |

TABLE 5-continued

| | | | | | | | |
|---|---|---|---|---|---|---|---|
| Component (A)-8 | | | | | | | |
| Component (A)-9 | | | | | | | |
| Component (A)-10 | | | | | | | |
| Component (A)-11 | | | | | | | |
| Component (A)-12 | | | | | | | |
| Component (B)-1 | 0.5 | 0.5 | | 0.1 | | 0.5 | 0.5 |
| Component (B)-2 | | | 0.5 | | 2.5 | | |
| Stearic acid | 10 | 10 | 10 | 10 | 10 | 10 | 10 |
| Cetyl alcohol | 7.5 | 7.5 | 7.5 | 7.5 | 7.5 | 7.5 | 7.5 |
| Squalane | 45 | 45 | 45 | 45 | 45 | 45 | 45 |
| Glyceryl tri-2-ethyl hexanoate | 10 | 10 | 10 | 10 | 10 | 10 | 10 |
| Sorbitan monooleate | 10 | 10 | 10 | 10 | 10 | 10 | 10 |
| Triethanol amine | 5 | 5 | 5 | 5 | 5 | 5 | 5 |
| Purified water | Balance | Balance | Balance | Balance | Balance | Balance | Balance |
| Total | 500 | 500 | 500 | 500 | 500 | 500 | 500 |

| | Example 19 Cosmetic composition 8 | Example 20 Cosmetic composition 9 | Example 21 Cosmetic composition 10 | Example 22 Cosmetic composition 11 | Example 23 Cosmetic composition 12 | Example 24 Cosmetic composition 13 |
|---|---|---|---|---|---|---|
| Component (A)-1 | | | | | | |
| Component (A)-2 | | | | | | |
| Component (A)-3 | 5 | | | | | |
| Component (A)-4 | | 5 | | | | |
| Component (A)-5 | | | 5 | | | |
| Component (A)-6 | | | | 5 | | |
| Component (A)-7 | | | | | 5 | |
| Component (A)-8 | | | | | | 5 |
| Component (A)-9 | | | | | | |
| Component (A)-10 | | | | | | |
| Component (A)-11 | | | | | | |
| Component (A)-12 | | | | | | |
| Component (B)-1 | | 0.5 | 0.5 | 0.5 | 0.5 | 0.5 |
| Component (B)-2 | 0.5 | | | | | |
| Stearic acid | 10 | 10 | 10 | 10 | 10 | 10 |
| Cetyl alcohol | 7.5 | 7.5 | 7.5 | 7.5 | 7.5 | 7.5 |
| Squalane | 45 | 45 | 45 | 45 | 45 | 45 |
| Glyceryl tri-2-ethyl hexanoate | 10 | 10 | 10 | 10 | 10 | 10 |

TABLE 5-continued

| | | | | | | |
|---|---|---|---|---|---|---|
| Sorbitan monooleate | 10 | 10 | 10 | 10 | 10 | 10 |
| Triethanol amine | 5 | 5 | 5 | 5 | 5 | 5 |
| Purified water | Balance | Balance | Balance | Balance | Balance | Balance |
| Total | 500 | 500 | 500 | 500 | 500 | 500 |

TABLE 6

| | Comp. Example 8 Cosmetic composition 14 | Comp. Example 9 Cosmetic composition 15 | Comp. Example 10 Cosmetic composition 16 | Comp. Example 11 Cosmetic composition 17 | Comp. Example 12 Cosmetic composition 18 | Comp. Example 13 Cosmetic composition 19 | Comp. Example 14 Cosmetic composition 20 |
|---|---|---|---|---|---|---|---|
| Component (A)-1 | | | | | | | |
| Component (A)-2 | | | | | | | |
| Component (A)-3 | | | | | | | |
| Component (A)-4 | | | | | | | |
| Component (A)-5 | | | | | | | |
| Component (A)-6 | | | | | | | |
| Component (A)-7 | | | | | | | |
| Component (A)-8 | | | | | | | |
| Component (A)-9 | 5 | | | | | | |
| Component (A)-10 | | 5 | 5 | | | | |
| Component (A)-11 | | | | 5 | | | |
| Component (A)-12 | | | | | 5 | | |
| Component (B)-1 | 0.5 | 0.5 | | 0.5 | 0.5 | 0.5 | |
| Component (B)-2 | | | 0.5 | | | | 0.5 |
| Stearic acid | 10 | 10 | 10 | 10 | 10 | 10 | 10 |
| Cetyl alcohol | 7.5 | 7.5 | 7.5 | 7.5 | 7.5 | 7.5 | 7.5 |
| Squalane | 45 | 45 | 45 | 45 | 45 | 45 | 45 |
| Glyceryl tri-2-ethyl hexanoate | 10 | 10 | 10 | 10 | 10 | 10 | 10 |
| Sorbitan monooleate | 10 | 10 | 10 | 10 | 10 | 10 | 10 |
| Triethanol amine | 5 | 5 | 5 | 5 | 5 | 5 | 5 |
| Purified water | Balance | Balance | Balance | Balance | Balance | Balance | Balance |
| Total | 500 | 500 | 500 | 500 | 500 | 500 | 500 |

<Cosmetic Composition Performance Evaluations>

The cosmetic compositions shown in Tables 5 and 6 above were evaluated in terms of (4) salt resistance in terms of viscosity, (5) temperature stability in terms of viscosity, (6) texture (gelatinous texture or the like) when used, and (7) temporal stability upon emulsification. Evaluation criteria are as described below. Moreover, viscosity measurements were carried out using a B type viscometer (a TVB-10 available from Toki Sangyo Co., Ltd.).

(4) Salt Resistance in Terms of Viscosity 0.5 g of NaCl was added to 100 g of a cosmetic composition shown in Table 5 or Table 6, and then stirred and mixed. The viscosity at 25° C. before and after the salt was added were measured and the salt resistance in terms of viscosity was evaluated. The evaluation was carried out on the basis of the criteria below. In these evaluations, B or higher was taken to be a pass.

A: Degree of change in viscosity of less than 5%

B: Degree of change in viscosity of not less than 5% but less than 10%

C: Degree of change in viscosity of not less than 10% but less than 30%

D: Degree of change in viscosity of not less than 30% but less than 50%

E: Degree of change in viscosity of not less than 50%

(5) Temperature Stability in Terms of Viscosity 100 g of samples shown in Tables 5 and 6 were placed in transparent glass containers and stored for 2 months in constant temperature baths at temperatures of 25° C. or 50° C. The state (viscosity) of each sample was then measured at 25° C., and the difference between the viscosity of a sample stored at 25° C. (standard value) and the viscosity of a sample stored at 50° C. was calculated as the degree of change in viscosity from these results, and evaluated as A to D, as shown below. In these evaluations, B or higher was taken to be a pass.

A: The degree of change in the viscosity of a sample stored at 50° C. compared to that of a sample stored at 25° C. was not more than 10%.

B: The degree of change in the viscosity of a sample stored at 50° C. compared to that of a sample stored at 25° C. was more than 10% but not more than 20%.

C: The degree of change in the viscosity of a sample stored at 50° C. compared to that of a sample stored at 25° C. was more than 20% but not more than 30%.

D: The degree of change in the viscosity of a sample stored at 50° C. compared to that of a sample stored at 25° C. was more than 30%.

(6) Texture when Used (Gelatinous Texture or the Like)

Specifically, a good texture (a gelatinous texture or the like) when used means (I) a soft gelatinous texture when approximately 5 g of an obtained sample is placed in the palm of the hand and shaken back and forth and also (II) a soft sample that can be easily spread when the sample is spread across the skin. The samples shown in Tables 5 and 6 were comprehensively evaluated in terms of items (I) and (II) above by 10 people, with the highest score being 5 points (and the lowest score being 1 point), and the total scores were evaluated as A to E using the criteria below. In these evaluations, B or higher was taken to be a pass.

A: Total score of 45 to 50 points

B: Total score of 40 to 44 points

C: Total score of 35 to 39 points

D: Total score of 30 to 34 points

E: Total score of 29 points or less (7) Temporal Stability upon Emulsification 100 g of a prepared cosmetic composition was stored for 3 months at 50° C., after which the emulsified state of the composition was observed. The evaluation was carried out on the basis of the criteria below. In these evaluations, B or higher was taken to be a pass.

A: Good emulsified state (no separation)

B: Fairly good emulsified state (some separation)

C: Poor emulsified state (separation into two layers)

TABLE 7

| | Salt resistance in terms of viscosity | Temperature stability in terms of viscosity | Texture when used | Temporal stability upon emulsification |
|---|---|---|---|---|
| Example 12 | A | A | A | A |
| Example 13 | A | A | B | A |

TABLE 7-continued

| | Salt resistance in terms of viscosity | Temperature stability in terms of viscosity | Texture when used | Temporal stability upon emulsification |
|---|---|---|---|---|
| Example 14 | A | A | A | A |
| Example 15 | A | B | A | B |
| Example 16 | A | A | B | A |
| Example 17 | A | A | A | A |
| Example 18 | A | A | A | A |
| Example 19 | A | A | A | A |
| Example 20 | A | A | B | A |
| Example 21 | A | A | A | A |
| Example 22 | A | A | B | A |
| Example 23 | A | A | B | A |
| Example 24 | A | A | A | A |

TABLE 8

| | Salt resistance in terms of viscosity | Temperature stability in terms of viscosity | Texture when used | Temporal stability upon emulsification |
|---|---|---|---|---|
| Comp. Example 8 | B | B | C | C |
| Comp. Example 9 | B | B | C | C |
| Comp. Example 10 | B | B | C | C |
| Comp. Example 11 | B | C | C | |
| Comp. Example 12 | C | C | C | C |
| Comp. Example 13 | C | C | C | C |
| Comp. Example 14 | E | B | E | B |
| Comp. Example 14 | E | B | E | B |

It was understood from the results that the product of this invention is a cosmetic composition that is favorable in terms of all of (4) salt resistance in terms of viscosity, (5) temperature stability in terms of viscosity, (6) texture when used, and (7) temporal stability upon emulsification.

INDUSTRIAL APPLICABILITY

The product of this invention is a cosmetic composition which exhibits improved performance compared to conventionally known cosmetic compositions, has high salt resistance and temperature stability in terms of the viscosity thereof, exhibits high temporal stability upon emulsification, and imparts a favorable texture when used. From a user's point of view, this cosmetic composition exhibits excellent feeling of use, and therefore meets high expectations and is extremely useful.

The invention claimed is:

1. A method for producing an aqueous gelling agent represented by general formula (1) below, the method comprising: adding an alcohol compound represented by general formula (2) at a molar ratio of 1.5 to 2.4 and a polyalkylene glycol represented by general formula (3) at a molar ratio of 0.5 to 1.4 to a diisocyanate compound represented by general formula (4) at a molar ratio of 2, and allowing these components to react in the presence of a higher fatty acid metal salt;

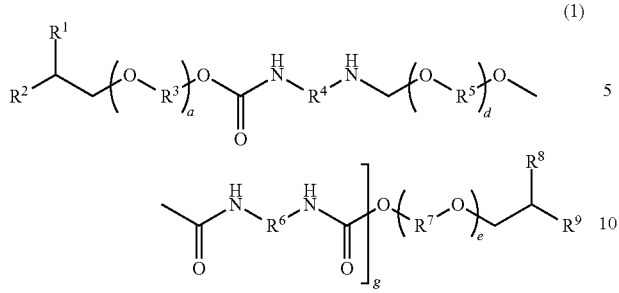
(1)

wherein $R^1$, $R^2$, $R^8$ and $R^9$ each independently denote a hydrocarbon group having 4 to 20 carbon atoms, $R^3$, $R^5$ and $R^7$ each denote represent a divalent hydrocarbon group having 2 to 4 carbon atoms, $R^4$ and $R^6$ each independently denote a divalent hydrocarbon group having 3 to 16 carbon atoms, a and e each independently denote a number from 10 to 100, d denotes a number from 100 to 500, and g denotes a number from 0 to 10;

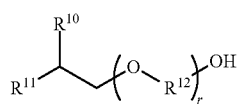
(2)

wherein $R^{10}$ and $R^{11}$ each independently denote a hydrocarbon group having 4 to 20 carbon atoms; $R^{12}$ denotes a divalent hydrocarbon group having 2 to 4 carbon atoms; and r denotes a number from 10 to 100;

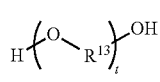
(3)

wherein $R^{13}$ denotes a divalent hydrocarbon group having 2 to 4 carbon atoms, and t denotes a number from 100 to 500; and

OCN-Q-NCO (4)

wherein Q denotes a divalent hydrocarbon group having 3 to 16 carbon atoms.

2. The method according to claim 1, wherein the higher fatty acid metal salt is one or more kinds of higher fatty acid metal salts selected from the group consisting of lauric acid metal salts, myristic acid metal salts, palmitic acid metal salts, stearic acid metal salts and oleic acid metal salts.

3. The method according to claim 1, wherein the higher fatty acid metal salt is a lauric acid metal salt.

4. The method according to claim 1, wherein the aqueous gelling agent is used in order to produce a cosmetic composition.

5. A method for producing a cosmetic composition, comprising:
a step of obtaining an aqueous gelling agent represented by general formula (1) below by adding an alcohol compound represented by general formula (2) at a molar ratio of 1.5 to 2.4 and a polyalkylene glycol represented by general formula (3) at a molar ratio of 0.5 to 1.4 to a diisocyanate compound represented by general formula (4) at a molar ratio of 2, and allowing these components to react in the presence of a higher fatty acid metal salt, and
and a step of combining said aqueous gelling agent and a polymeric thickening agent;

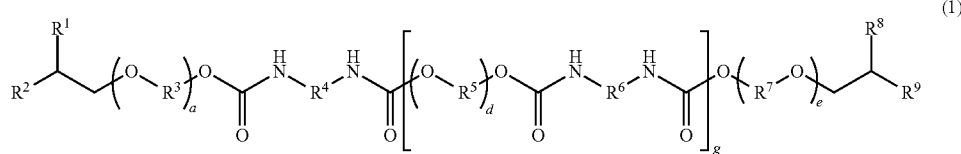
(1)

wherein $R^1$, $R^2$, $R^8$ and $R^9$ each independently denote a hydrocarbon group having 4 to 20 carbon atoms, $R^3$, $R^5$ and $R^7$ each denote represent a divalent hydrocarbon group having 2 to 4 carbon atoms, $R^4$ and $R^6$ each independently denote a divalent hydrocarbon group having 3 to 16 carbon atoms, a and e each independently denote a number from 10 to 100, d denotes a number from 100 to 500, and g denotes a number from 0 to 10;

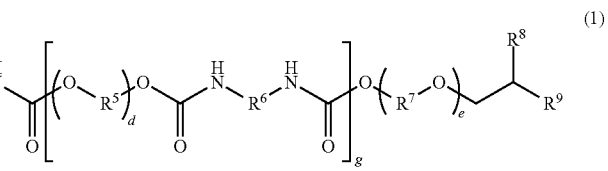
(2)

wherein $R^{10}$ and $R^{11}$ each independently denote a hydrocarbon group having 4 to 20 carbon atoms, $R^{12}$ denotes a divalent hydrocarbon group having 2 to 4 carbon atoms, and r denotes a number from 10 to 100;

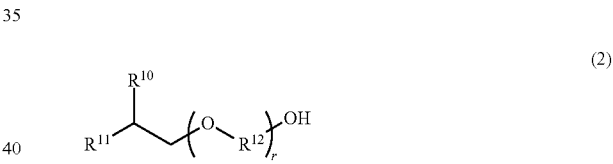
(3)

wherein $R^{13}$ denotes a divalent hydrocarbon group having 2 to 4 carbon atoms, and t denotes a number from 100 to 500; and

OCN-Q-NCO (4)

wherein Q denotes a divalent hydrocarbon group having 3 to 16 carbon atoms.

6. The method according to claim 2, wherein the aqueous gelling agent is used in order to produce a cosmetic composition.

7. The method according to claim 3, wherein the aqueous gelling agent is used in order to produce a cosmetic composition.

* * * * *